US012708484B2

(12) United States Patent
Angulo Renteria

(10) Patent No.: US 12,708,484 B2
(45) Date of Patent: Aug. 18, 2026

(54) PNEUMATIC DEVICE FOR WASHING, DRYING AND DISINFECTION ENDOSCOPES AND METHODS FOR DETECTING OBSTRUCTIONS AND LEAKS IN AN ENDOSCOPE

(71) Applicant: RUVID S.A.S., Cali (CO)

(72) Inventor: Francisco Javier Angulo Renteria, Cali (CO)

(73) Assignee: RUVID S.A.S., Cali (CO)

( * ) Notice: Subject to any disclaimer, the term of this patent is extended or adjusted under 35 U.S.C. 154(b) by 784 days.

(21) Appl. No.: 17/907,074

(22) PCT Filed: Oct. 30, 2021

(86) PCT No.: PCT/IB2021/060069

§ 371 (c)(1),
(2) Date: Sep. 22, 2022

(87) PCT Pub. No.: WO2022/123344

PCT Pub. Date: Jun. 16, 2022

(65) Prior Publication Data

US 2024/0000541 A1 Jan. 4, 2024

(30) Foreign Application Priority Data

Dec. 9, 2020 (CO) ............................ 2020/0015390

(51) Int. Cl.
*A61B 90/70* (2016.01)
*A61B 1/015* (2006.01)
(Continued)

(52) U.S. Cl.
CPC .............. *A61B 90/70* (2016.02); *A61B 1/015* (2013.01); *A61B 1/125* (2013.01); *A61L 2/24* (2013.01); *A61B 2090/701* (2016.02)

(58) Field of Classification Search
CPC ................................. A61L 2/18; A61B 90/70
See application file for complete search history.

(56) References Cited

U.S. PATENT DOCUMENTS 4,752,444 A * 6/1988 Bowen ................ A61C 19/002
422/292

FOREIGN PATENT DOCUMENTS

WO WO-2019123268 A1 * 6/2019

OTHER PUBLICATIONS

English Translation of International Publication No. WO 2019/123268 A1 provided by the European Patent Office website espacenet.com: Angulo Renteria Francisco; Pneumatic Device for Washing and Disinfecting Endoscopes; Jun. 27, 2019 (Year: 2019).*

* cited by examiner

*Primary Examiner* — Kevin Joyner
(74) *Attorney, Agent, or Firm* — The Morales Law Firm; Joseph L. Morales

(57) ABSTRACT

The present invention relates to a pneumatic device for washing, disinfecting, and drying medical device canals and methods for detecting obstructions and leaks by means of pneumatic systems (e.g., a double-acting pneumatic cylinder), with which fluids and a pressurized gas are mobilized, a computing unit for monitoring control elements and a multi-way valve. Preferably, the device comprises a mechanical multi-way valve to control the direction of the fluids and the pressurized gas entering the pneumatic device for washing, disinfecting, and drying medical device canals. This allows to carry out the washing, disinfection and drying of at least one of the canals of a medical device and detect obstructions and leaks of the same canal saving energy and using little space, compared to devices that use hydraulic systems generating large sizes and high energy consumption.

14 Claims, 7 Drawing Sheets

(51) Int. Cl.

| | |
|---|---|
| ***A61B 1/12*** | (2006.01) |
| ***A61L 2/18*** | (2026.01) |
| ***A61L 2/24*** | (2006.01) |

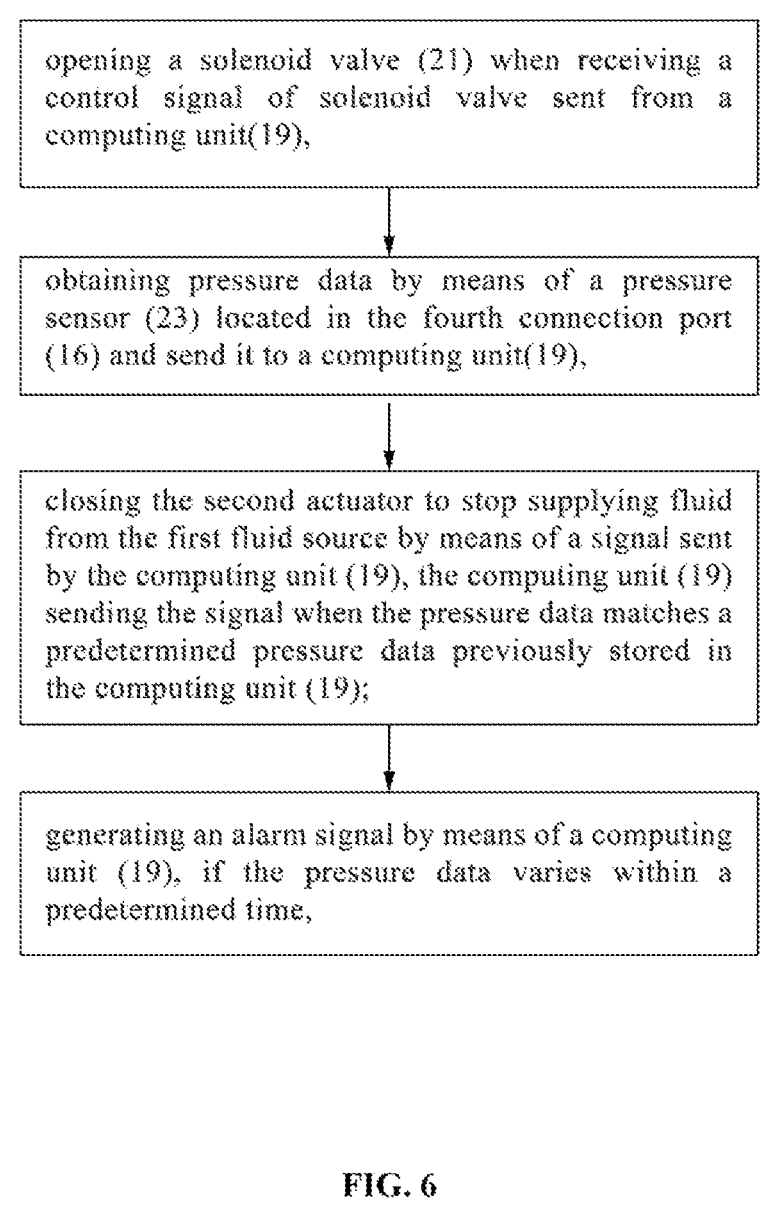

opening a solenoid valve (21) when receiving a control signal of solenoid valve sent from a computing unit(19),

↓ obtaining pressure data by means of a pressure sensor (23) located in the fourth connection port (16) and send it to a computing unit(19),

↓ closing the second actuator to stop supplying fluid from the first fluid source by means of a signal sent by the computing unit (19), the computing unit (19) sending the signal when the pressure data matches a predetermined pressure data previously stored in the computing unit (19);

↓ generating an alarm signal by means of a computing unit (19), if the pressure data varies within a predetermined time,

FIG. 6

PNEUMATIC DEVICE FOR WASHING, DRYING AND DISINFECTION ENDOSCOPES AND METHODS FOR DETECTING OBSTRUCTIONS AND LEAKS IN AN ENDOSCOPE

FIELD OF INVENTION

The present invention relates to a device for cleaning and disinfecting device canals. Particularly, the present invention relates to a device for leak testing, cleaning, disinfecting, and drying an endoscope.

DESCRIPTION OF THE PRIOR ART

The present disclosure relates to devices for cleaning and disinfecting device canals, mainly medical devices. Particularly in those medical devices having canals that are narrow such as, an endoscope, bronchoscope, bronchoscope, colonoscope, cystoscope, duodenoscope, stereoscope, gastroscope, arthroscopes, urethroscope, laparoscope, and other instruments that internally contain narrow canals.

Currently these types of medical devices are used for the visual exploration of ducts or internal cavities of the human body and given their functionalities and their contribution to medical science, they are used on a daily basis for surgical procedures, diagnostic methods, and other medical practices.

In particular, the endoscope is a useful, complex and reusable instrument, which means that it inevitably requires appropriate washing and disinfection techniques to ensure that the patients on whom it is to be used have the certainty it will not be a source of infections, bacteria and viruses, because endoscopy, as an invasive procedure, is in itself an intrinsic risk factor, acting as an indirect contact route for the transmission of microorganisms.

Previously, for the washing and disinfection of endoscopes, specialized personnel had to manually clean the endoscopes, but considering the constant use of endoscopes in the medical sector, advances, improvements, and new inventions have been made regarding the decontamination of these devices.

Nowadays, automated endoscope reprocessors are used for cleaning, disinfection, and sterilization of endoscopes, which wash, disinfect, and sterilize the endoscope with different or the same cleaning agents. Additionally, some of these reprocessors use different systems for drying after cleaning, disinfection, and sterilization.

Disclosures such as EP1779770, WO2005/05606060, EP1757313, and ES2324551 are identified in the prior art, which relate to devices for cleaning narrow lumen medical devices using hydraulic or centrifugal pumps whose mission is to pump liquids through the canals of an endoscope. On the other hand, different systems are used to dry these devices in order to get air into the canals of the endoscope.

Now, these units are robust, and most cases have impellers. Additionally, they require exhaust or ventilation systems to cool the internal components of the equipment. As a result, these devices generate a high energy demand and have a large size.

Finally, these devices do not detect obstructions or leaks in the endoscope, which could avoid increased washing and drying time and increased energy demand.

Therefore, there is a need for devices that can carry out cleaning, disinfection, sterilization, and drying taking up little space and low energy demand, as well as detecting obstructions and leaks in the endoscope.

Document CO34800 solves this technical problem with a pneumatic endoscope washing device for the supply and/or pumping of liquids that incorporates a linear pneumatic system that converts the compressed air inside the cylinder into kinetic energy, incorporating a syringe for the storage of liquids and air. In this way, a piston-type suction and compression of liquids is generated, which displaces the fluid to the surface in the upward or downward stroke, generating a pressure oscillation that overlaps the cleaning fluid. And by means of special connectors that reach the internal canals of the endoscope, a general sweep of microorganisms is generated by means of liquids and pressurized air, which effectively carries out the washing and disinfection.

However, the prior art does not disclose a device that allows independent drying and allows detection of obstructions or leaks in medical device canals. Additionally, the prior art does not disclose devices that take up little space and generate little energy demand, and that, in addition, avoid increased cleaning, disinfection and drying times.

BRIEF DESCRIPTION OF THE DISCLOSURE

The present disclosure relates to a pneumatic device for washing, drying, and disinfecting device canals, comprising a cylinder comprising a chamber having a fluid inlet and an outlet, said inlet configured to connect to a first fluid source, a rod connected to the outlet and a plunger arranged on the rod, said plunger being located within the chamber.

Additionally, the device for washing, drying, and disinfecting medical device canals comprises a plunger connected to one end of the stem and a container with an inlet and an outlet. The inlet of the container is aligned with the outlet of the chamber and wherein the piston is located inside the container.

On the other hand, the device for washing, drying, and leak-proof disinfecting device canals, comprises a multi-way valve with four connection ports, a first connection port configured to connect to a container outlet; a second connection port configured to connect to a second fluid source; a third connection port configured to connect to a device canal; and a fourth connection port configured to connect to the first fluid source.

In particular, the chamber inlet allows the entry of a gas from the first fluid source into the chamber generating a fluid pressure difference inside the chamber, which causes an up and down movement of the plunger.

On the other hand, the multi-way valve in a first position allows the passage of fluid from the second fluid source to the container; in a second position it allows the passage of fluid from the container to the device canal; and in a third position it allows the passage of fluid from the first fluid source to the device canal.

In another aspect of the disclosure, it relates to a method of detecting obstructions in device canals by means of the device for washing, drying, and disinfecting device canals, comprising: periodically opening a first actuator according to an activation time and a return time, starting from a first actuation control signal sent by a computing unit connected to the first actuator, wherein said first actuator is located between the inlet and the gas source obtaining a plunger position data by means of the computing unit and generating a second actuation control signal, by means of the computing unit, starting from a cycle time from the position data.

In particular, the opening of the first actuator allows the entry of fluid from the first fluid source, which generates a fluid pressure difference inside the chamber to generate an up and down movement of the plunger. The second actuation control signal decreases the activation time, thereby increasing the speed of movement of the plunger and in turn the piston rod and piston. As a result, the pressure exerted on the fluid entering the device canal is increased, thereby releasing the obstructions.

In another aspect of the disclosure, it relates to a method of detecting device canal leaks using a device canal flushing, drying and disinfection device comprising: opening a second actuator upon receiving an actuation control signal sent by a computing unit, said second actuator arranged between a first fluid source and a fourth connection port of the multi-way valve obtaining a pressure data by means of a pressure sensor located in the fourth connection port and sending it the computing unit, the pressure sensor being connected to the computing unit; close the second actuator to stop supplying gas from the gas source, by means of a signal sent by the computing unit, the computing unit sends the signal when the pressure data matches a previously predetermined pressure data stored in the computing unit; and generate an alarm signal, by means of the computing unit, if the pressure data varies within a predetermined time after the closing of the second actuator.

In particular, the multi-way valve is in a third position, which allows the passage of fluid from the first fluid source into the canal of the medical device.

BRIEF DESCRIPTION OF THE FIGURES

FIG. 1A shows a plunger of the pneumatic cylinder in the end stroke position and FIG. 1B shows the plunger of the pneumatic cylinder in the initial stroke position.

FIG. 6 shows a flow diagram of a device canal leak detection method.

DETAILED DESCRIPTION OF THE INVENTION

The present invention is directed to a device for washing, drying, and disinfecting device canals, wherein said device for washing, drying, and disinfecting device canals inserts a pressurized gas or fluid into a canal of a device, which may be a medical device (e.g., an endoscope, bronchoscope, colonoscope, cystoscope, duodenoscope, stereoscope, gastroscope, arthroscope, urethroscope, laparoscope, and other instruments that internally contain narrow canals) that may be tight or narrowed, for washing, drying, or disinfecting depending on the need. On the other hand, the device for washing, drying, and disinfecting device canals of the present disclosure uses a pressurized fluid delivered by a first fluid source, which may be a gas source (5). The pressurized fluid enters a cylinder with a piston rod, which may be a pneumatic cylinder (1), and said cylinder uses said pressurized fluid to move a piston rod which in turn moves a fluid, which is inserted into the device canal (40). On the other hand, the same pressure fluid, which in this case would be a gas, can also be used to be inserted into the device canal (40) for drying the device. In one embodiment of the disclosure, the first fluid source is a liquid source, and the cylinder is a hydraulic cylinder.

On the other hand, a tight or narrow canal is considered a canal measuring less than 6 mm, so conventional cleaning, disinfection, and drying methods are not able to clean these canals adequately for medical use.

Figure 1A:
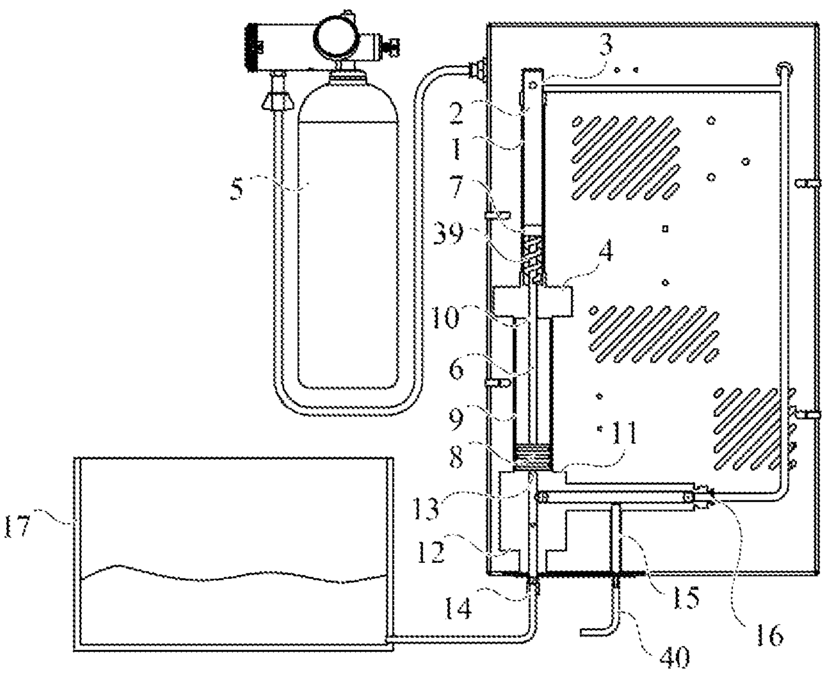
FIGS. 1A and 1B show one embodiment of a pneumatic device for washing, drying, and disinfecting device canals comprising: a single-acting pneumatic cylinder, a container, a plunger, a fluid source, a multi-way valve and a gas source. Particularly.
Figure 1B:
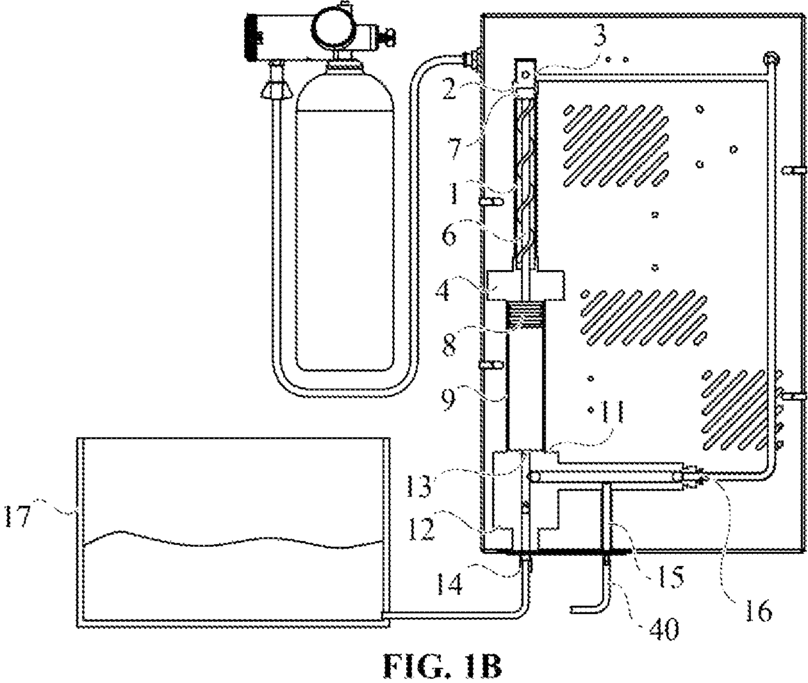

Referring to FIGS. 1A and 1B, in a preferred embodiment of the invention, the canal device (100), comprises:

- a pneumatic cylinder (1) consisting of:
  - a chamber (2) with an inlet (3) and an outlet (4), said inlet (3) being configured to connect with the gas source (5)
  - a piston rod (6) connected to the outlet (4); and
  - a plunger (7) arranged on the piston rod (6), said plunger (7) being located inside the chamber (2);
- a piston (8) connected to one end of the piston rod (6);
- a container (9) with an inlet (10) and an outlet (11), said inlet (10) being aligned with the outlet (4) of the pneumatic cylinder (1) wherein the piston (8) is located inside the container (9); and
- a multi-way valve (12) with four connection ports, a first connection port (13) configured to connect to the outlet (11) of the container (9); a second connection port (14) configured to connect to a second fluid source (17); a third connection port (15) configured to connect to a canal (40) of a device; and a fourth connection port (16) configured to connect to the gas source (5).

In the device for washing, drying, and disinfecting device canals (100) of the present disclosure, the inlet (3) of the chamber (2) allows the entry of a gas coming from the gas source (5) into the chamber (2), generating a gas pressure difference inside the chamber (2), to generate an upward and downward movement of the plunger (7).

On the other hand, the multi-way valve (12) in a first position, it allows the passage of the fluid coming from the second fluid source (17) into the container (9); in a second position, it allows the passage of the fluid from the container (9) into the device canal (40); and in a third position, it allows the passage of the gas from the gas source (5) into the device canal (40).

Particularly, the device for washing, drying, and disinfecting device canals (100) of the present disclosure carries out the washing and disinfecting by moving a fluid from the second fluid source (17) into the device canal (40).

The fluid movement is made by means of the pneumatic cylinder (1) and the piston (8), wherein the piston (8) moves upwardly when the fluid is sucked from the second fluid source (17) into the container (9). At this first moment, the multi-way valve (12) is in the first position. This means that the fluid enters through the second connection port (14) and exits through the first connection port (13). Then, the piston (8) moves downwards so the fluid that was in the container (9) moves from the container (9) to the device canal (40). At this second moment, the multi-way valve (12) is in the second position, i.e., the fluid enters through the first connection port (13) and exits through the third connection port (15).

Upward movement should be understood as the movement of the piston (8) and the plunger (7), when these elements move from the outlet to the inlet of the container where they are arranged, i.e., in the case of the plunger (7), the upward movement is when the plunger (7) moves from the outlet (4) towards the inlet (3). On the contrary, the downward movement should be understood as the movement of the piston (8) and the plunger (7), where these elements move from the inlet to the outlet of the container or chamber (2) where they are arranged, i.e., in the case of the plunger (7), the downward movement is when the plunger (7) moves from the inlet (3) towards the outlet (4).

As mentioned above, the pneumatic cylinder (1) is in charge of moving the piston (8) in order to control the movement of the fluid that can be found inside the container (9). The pneumatic cylinder (1) uses the pressurized gas sent by the gas source (5) to move the piston (7) which in turn moves the piston rod (6) that is connected to the piston (7), said pressurized gas enters through the inlet (3). On the other hand, the pneumatic cylinder (1) can have one inlet (3) or several inlets (3), the number of inlets (3) will depend on the type of cylinder, e.g., if the pneumatic cylinder (1) is a single acting cylinder, only one inlet (3) is needed. On the other hand, if the pneumatic cylinder (1) is double acting, two inlets (3) will be required.

In one embodiment of the disclosure, the pneumatic cylinder (1) is single acting. In this case the pneumatic cylinder (1) has a single inlet (3), through which it enters and exits the pressurized gas coming from the gas source (5). In this embodiment, the piston (7) is connected to an elastic element, said elastic element is arranged between the piston (7) and the outlet (4). The pressurized gas first enters the chamber (2) through the inlet (3). As a result, the plunger (7) moves downwards to generate a compression in the elastic element. Once the plunger (7) is in the end position, the pressurized gas is prevented from entering through the inlet (3) and consequently the elastic element moves the plunger (7) to an initial position.

It should be understood as initial position when the plunger (7) is located in the closest position to the inlet (3), on the other hand, it should be understood as final position when the plunger (7) is located in the closest position to the outlet (4). Furthermore, the term cycle time should be understood as the time it takes for the plunger (7) to start its movement from the initial position, travel to the final position and return to the initial position. On the other hand, the term stroke cycle should be understood as the movement of the piston (7) from the initial position to the final position and back to the initial position. On the other hand, half stroke cycle is considered as the stroke since the piston (7) starts its movement from the initial position and travels to the final position.

Referring to FIG. 1, the device for washing, drying, and disinfecting device canals (100) has a single acting pneumatic cylinder (1), wherein the pneumatic cylinder (1) comprises a chamber (2) which has a single inlet (3) connected to the gas source (5) and an outlet (4) through which the piston rod (6) exits. The rod (6) at one end has the piston (8) and at the other end has the plunger (7), said plunger (7) arranged inside the chamber (2). Additionally, an elastic element (39), which in this case is a spring, is arranged coaxially regarding the piston rod (6) and between the plunger (7) and the outlet (4) of the chamber (2). One of the technical effects of using a single-acting cylinder is that it allows less control devices to be used, since this configuration is more easily controlled.

In another embodiment of disclosure, the pneumatic cylinder (1) is double acting, in this case the pneumatic cylinder (1) has two inlets (3), through which the pressurized gas from the gas source (5) enters alternately, i.e., pressurized gas never enters through two inlets (3) at the same time. In this embodiment, the plunger (7) divides the chamber (2) into two chambers, a first chamber and a second chamber, wherein each chamber has an inlet (3) and in the second chamber there is the outlet (4), and when the pressurized gas enters one of the chambers through the inlet (3), the plunger (7) moves upward or downward respectively. When pressurized gas enters the first chamber, the plunger (7) moves downwardly and when the plunger (7) reaches the end position, pressurized gas is prevented from entering through the inlet (3) of the first chamber and pressurized gas is allowed to enter through the inlet (3) of the second chamber. When pressurized gas enters the second chamber, the piston (7) moves upward, and the gas reaches its initial position again.

Figure 3:
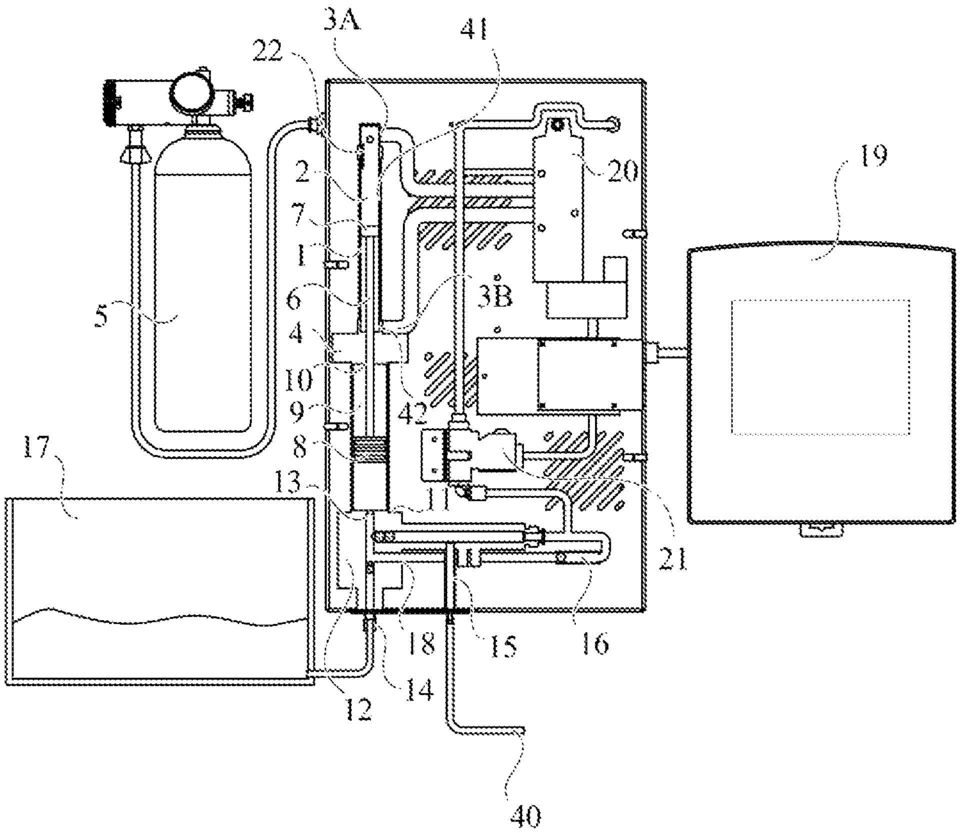
FIG. 3 shows one embodiment of a pneumatic device for washing, drying, and disinfecting device canals comprising a double-acting pneumatic cylinder, a container, a piston, a fluid source, a multi-way valve, two solenoid valves and a gas source.
Figure 4:
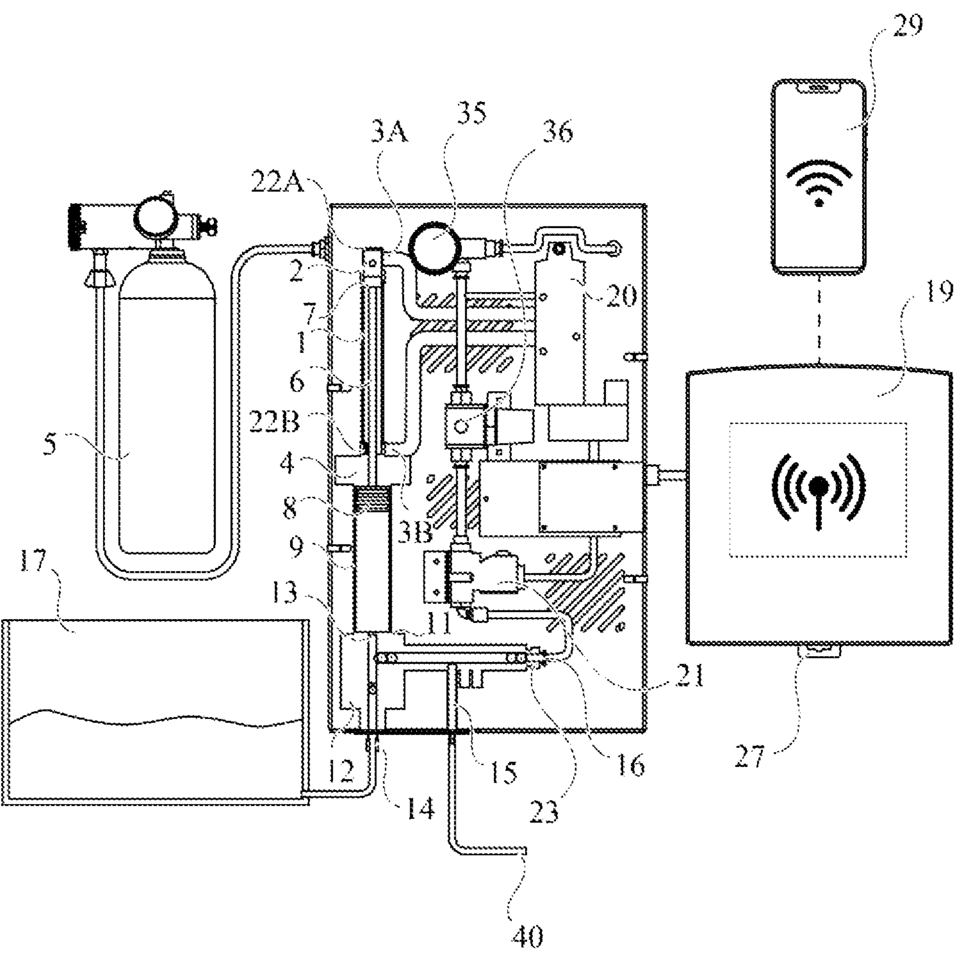
FIG. 4 shows one embodiment of a pneumatic device for device canals comprising a double-acting pneumatic cylinder, two presence sensors, a container, a piston, a fluid source, a multi-way valve, two solenoid valves, a pressure gauge, a flowmeter, a gas source and a computing unit.

Referring to FIGS. 3 and 4, the device for washing, drying, and disinfecting device canals (100) has a double-acting pneumatic cylinder (1), wherein the pneumatic cylinder comprises a chamber (2), which has inlets (3A,3B) connected to the gas source (5) and an outlet (4) through which the piston rod (6) exits. The piston rod (6) at one end has the piston (8) and at the other end has the plunger (7), said plunger (7) arranged inside the chamber (2). The chamber (2) is divided into a first and a second chamber (41, 42), wherein the inlet (3A) is arranged in the first chamber (41), and the inlet (3B) and the outlet (4) are located in the second chamber (42). One of the technical effects of using a double-acting cylinder is that it allows to have control over both the upward movement of the piston (7) and the downward movement of the piston (7), which allows to have more control over the time in which the stroke cycle is carried out.

In another particular example, the cylinder is a hydraulic cylinder and in the same way as when it is a pneumatic cylinder (1), it can be double acting or single acting. In the same way, all the described modalities that refer to the pneumatic cylinder (1) are fulfilled for a hydraulic cylinder, the only difference is that in these modalities the fluid under pressure is not a gas but a liquid.

The inlet of the pressurized gas or pressurized fluid that moves the piston (7) of the cylinder, either the pneumatic cylinder (1) or a hydraulic cylinder, can be controlled by means of a flow control element located upstream of the cylinder inlet. Such a flow control element allows control of the pressure and time at which pressurized gas or pressurized fluid is inserted through the inlet (3). The control element may be a valve, an actuator (e.g., electromechanical actuator), a compressor or any control element known to a person ordinarily skilled in the art. Optionally, between the first fluid source and the inlet (3) a valve is arranged. More preferably between the gas source (5) and the inlet (3) a valve is arranged.

On the other hand, the fluid of the second fluid source (17) can be selected from liquids, such as water, detergent, disinfectants (Orthopthaldehyde and Glutaraldehyde), alcohols, and combinations thereof.

In another embodiment of the invention, the pneumatic device for washing, drying, and disinfecting device canals (100) of the present disclosure carries out the drying by entering pressurized gas coming from the first fluid source which in this case is a gas source (5) into the device canal (40). In another embodiment of the invention, the drying is done by entering pressurized gas coming from the second fluid source (17) which in this case is a gas source.

In the embodiment, when the first fluid source, which is the pressurized gas source (5), the pressurized gas enters the multi-way valve (12) and is directed to the device canal (40), the multi-way valve (12) is configured in the third position, i.e., the pressurized gas enters through the fourth connection port (16) and exits through the third connection port (15).

The foregoing means that the inflow of pressurized gas to the multi-way valve (12) for drying can be controlled by a flow control element upstream of the fourth connection port (14). Said flow control element allows to control the pressure and the time at which the pressurized gas enters the fourth connection port (14). Preferably, the pressurized gas enters the fourth connection port (14) of the multi-way valve (12) at a pressure between 20 Psi to 25 Psi. The control element may be a valve, an actuator (e.g., an electromechanical actuator), a compressor or any control element known to a person ordinarily skilled in the art. Optionally, between the first fluid source and the fourth connection port (14) a valve is arranged. More preferably, between the gas source (5) and the fourth connection port (14) a valve is arranged.

Optionally, in the present disclosure the valves are selected from the group consisting of solenoid valves, ball valves, check valves, gate valves, safety or pressure relief valves, globe (or poppet) valves, butterfly valves, diaphragm valves, rotary valves, non-return valves, such as swinging flap valves, spring valves, piston valves, ball check valves, knife gate valves, regulating and control valves and combinations thereof. Preferably, between the gas source (5) and the inlet (3) a valve is arranged, and between the gas source (5) and the fourth connection port (16) a valve is arranged.

In one embodiment of the invention, between the first fluid source, which may be the gas source (5), and the inlet (3) a first actuator is arranged. Additionally, between the first fluid source, which may be the gas source (5), and the fourth connection port (16) a second actuator is arranged and still more preferably said first actuator and second actuator are solenoid valves.

The multi-way valve (12) is a valve having several inlets and several outlets, wherein depending on an internal blocking element it allows controlling the direction of a fluid entering the valve. Specifically, the multi-way valve (12) controls the direction of the fluid coming from the second fluid source (17) and the pressurized gas coming from the gas source (5), depending on the position. The technical effect thereof is that by using the multi-way valve (12), cleaning, disinfection, and drying can be carried out without using different elements, which facilitates and reduces the time required to carry out these tasks.

The multi-way valve (12) can be selected from the group consisting of pneumatic multi-way valves, electro-pneumatic multi-way valves, electric multi-way valves, or mechanical multi-way valves and combinations thereof.

Referring to FIGS. 1, 2, 3, and 4, the multi-way valve (12) is a mechanical multi-way valve with ball bearings, said mechanical multi-way valve having canals inside. They are sealed with balls that move according to the flow of air or liquids entering through the connection ports of the multi-way valve (12), allowing the flow of fluids in one direction or another depending on the position of the balls. One of the technical effects of using the mechanical multi-way valve (12) with ball bearings is that it allows the fluid direction to be controlled without the need for control elements, thus reducing the energy load on the device for washing, drying, and disinfecting device canals (100).

Specifically, the balls move with the negative or positive flow currents generated by the movement of the piston (8) inside the container (9). The pressure exerted by these flow currents within the canals of the multi-way valve (12) are intended to direct the fluid. Either towards the container (9), having negative flow currents; or towards the device canal (40), having positive flow currents; depending on the position of the piston (8).

It is to be understood that the expression negative flow stream is when the plunger (7) moves upwardly at that moment a lower pressure is generated inside the container (9), whereby the fluid is drawn towards the inside of the container (9). On the other hand, the expression positive flow current is when the plunger (7) moves downwardly at this moment the fluid inside the container (9) is drawn towards the inside of the multi-way valve (12).

Figure 2A:
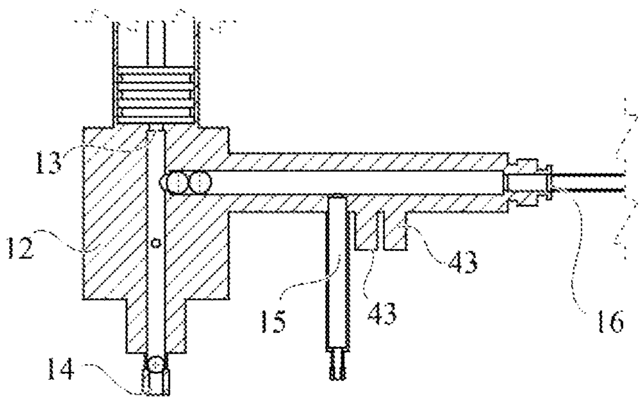
FIG. 2A shows one embodiment of a mechanical multi-way valve with a ball valve, wherein a fluid flows from a second connection port to a first connection port.
Figure 2B:
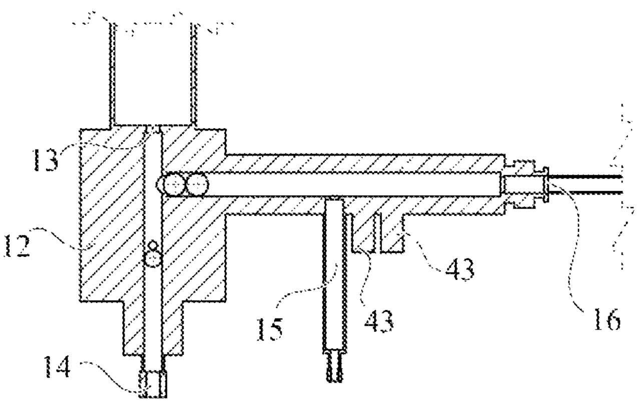
FIG. 2B shows one embodiment of a multi-way mechanical ball valve, wherein a fluid flows from the first connection port to a third connection port.
Figure 2C:
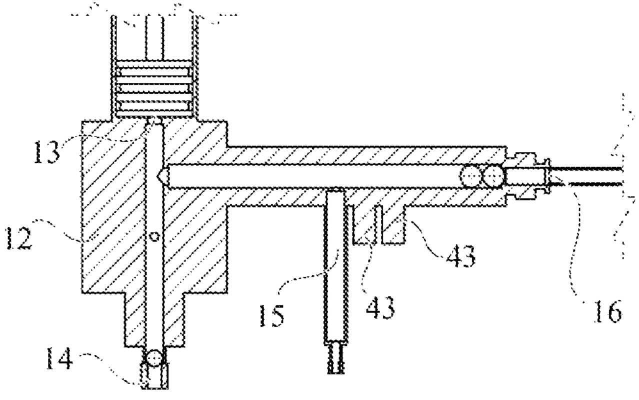
FIG. 2C shows one embodiment of a multi-way mechanical ball valve, wherein a pressurized gas flows from a fourth connection port to a third connection port.

Referring to FIGS. 2A, 2B, 2C, in one embodiment of the disclosure, the multi-way valve (12) comprises two internal canals, said canals are connected to each other and are orthogonal to each other. At the ends of the first canal, the first connection port (13) and the second connection port (14) are located. The second canal has the fourth connection port (16) at one end and is connected to the first canal at the opposite end. The third connection port (15) is located between the two ends of the second canal. In each internal canal a ball is located, which moves according to the fluid currents, the balls control the direction of the fluid according to their position.

Continuing with FIG. 2A, the multi-way valve (12) is shown in the first position, in this case the plunger (7) moves upwardly and generates a negative flow current, which causes the fluid coming from the second fluid source (17) and the first canal ball to move from the second connection port (14) to the first connection port (13), thus the fluid enters the container (9). In turn, the second canal ball moves to the end of the second canal that connects to the first canal, which end has a decrease in the internal diameter of the canal. The decrease in diameter prevents the ball from entering the first canal and closes the first canal, thus preventing the fluid that is moving towards the container (9) from entering the second canal, as well as preventing the fluid present in the second canal from entering the first canal.

FIG. 2B shows the multi-way valve (12) in the second position, in this case the plunger (7) moves downwards and generates a positive flow current, which causes the fluid that was in the container (9) to move towards the third connection port (15). In this case, the ball of the first canal moves towards the end of the first canal where the second connection port (14) is located, this end has a decrease in the internal diameter of the canal. The decrease in diameter prevents the ball from exiting the multi-way valve (12) and prevents the fluid coming from the container (9) from exiting through the second connection port (14).

On the other hand, in this case, the ball that is arranged in the second canal moves towards the end where the fourth connection port (16) is located, said end has a decrease in the internal diameter of the canal. The decrease in diameter prevents the ball from exiting the multi-way valve (12) and prevents the fluid coming from the container (9) from exiting through the fourth connection port (16).

Finally, being the balls at the ends with decreasing diameter, the fluid exits through the third connection port (15) and enters the medical device by means of the device canal (40).

Referring to FIG. 2B, the multi-way valve (12) is shown in the third position, in this case the pressurized fluid, which in this case is pressurized gas, coming from the first fluid source, which in this case is the gas source (5), enters through the fourth connection port (16) and exits through the third connection port (15). In this case, the ball located in the second canal moves toward the end that connects to the first canal, and similarly to the first position is arranged in the diameter decrease. In this case, the ball prevents the pressurized gas from going into the first canal, so the incoming pressurized gas exits only through the third connection port (15).

The multi-way valve (12) may have at least one connection port in addition to the four connection ports (13, 14, 15, 16). The more connection ports the multi-way valve (12) has, the more directions of fluid flow it controls, and the more canals of the medical device or different medical devices it can connect to.

In one embodiment of the disclosure, the multi-way valve (12) may have additional connection ports connected to the second canal and located between the fourth connection port (16) and the end of the second canal that connects to the first canal.

Referring to FIGS. 2A, 2B, 2C, the multi-way valve (12) has two additional connection ports (43), in the vicinity of the third connection port (15), said additional connection ports (43) allowing to make washing, drying and disinfection of several canals of one medical device or canals of different medical devices.

In a particular example and following FIGS. 2A, 2B, 2C, in the case where the medical device is an endoscope having a suction canal, an air canal, and a water canal. In this case, in order to wash said endoscope, the third connection port (15) can be connected to the suction canal, one of the additional connection ports (43) can be connected to the water canal and the other additional connection port (43) can be connected to the air canal.

Optionally, the device for washing, drying, and disinfecting device canals (100) can be provided with a coupling element, wherein the coupling element comprises an inlet and at least two outlets. In this case, the inlet of the coupling element is connected to the third connection port (15) and the outlets can be connected to at least two canals of one medical device or canals of different medical devices. In a non-illustrated embodiment, the medical device may be an endoscope having a suction canal, an air canal, and a water canal, wherein the coupling element is connected to the third connection port to wash said endoscope. In this case there are no additional ports, and the coupling element has three outlets. Therefore, one of the outlets of the coupling element can be connected to the suction canal, another outlet is connected to the water canal, and other outlets can be connected to the air canal.

Referring to FIG. 3, the multi-way valve (12) has a fifth connection port (18) connected to the first fluid source which in this case is the gas source (5), wherein the multi-way valve (12) has a fourth position, wherein the gas enters through the fifth connection port (18) and exits through the second connection port (14).

The addition of a fifth connection port (18) allows the drying of a connection element which may be a hose that connects to the second connection port (14), said connection element being the one that carries the fluid from the second fluid source (17) to the multi-way valve (12). Another advantage of adding the fifth connection port (18) is that when the device for washing, drying, and disinfecting device canals (100) of the present disclosure is drying the device canal (40), the pressurized gas entering through the second connection port (14) can also be directed to the fifth connection port (18), in addition it can also be directed towards the fifth connection port (18), whereby the drying of the device canal (40) and of the connecting element carrying the fluid from the second fluid source (17) to the multi-way valve (12) can be carried out simultaneously.

In one embodiment of the invention, when simultaneous drying of the canal (40) and the connecting element of the second fluid source (17) is to be carried out, and the multi-way valve (12) is a mechanical multi-way ball valve, the fifth connection port (18) is connected to the first canal of the multi-way valve (12). Consequently, the ball in the first canal should not be above the second connection port (14), therefore, the pneumatic cylinder (1) must be activated so the ball moves towards the first connection port (13). Once the first canal ball is not in the second connection port (14), the pressurized gas entering through the fifth connection port (18) exits the second connection port (14) towards the fluid source connection element. In turn, the ball located in the second canal moves towards the end that connects to the first canal. In this case, the ball prevents the pressurized gas from going into the first canal so that the pressurized gas entering the fourth connection port (16) exits only through the third connection port (15).

Referring to FIG. 3, in one embodiment of the disclosure, a one-way valve is located between the gas source (5) and the fifth connection port (18), wherein said one-way valve prevents fluid from the second fluid source (17) from being directed towards the gas source (5), when said fluid is directed towards the container (9).

In one embodiment of the invention, the one-way valve is located in the vicinity of the fifth connection port (18), it is preferable that the one-way valve is directly connected to the fifth connection port (18). The foregoing means that when fluid from the second fluid source (17) is directed toward the container (9), a portion of said fluid exits the multi-way valve (12) through the fifth connection port (18).

The device for washing, drying, and disinfecting device canals (100) of the present disclosure can carry out automatic cleaning, disinfection, and drying by means of a control system that controls pneumatic variables of the device, which controls when and how the fluid coming from the second fluid source (17) or the pressurized fluid coming from the first fluid source which preferably is the gas source (5) enters. In the present disclosure, the control system may comprise a computing unit, peripheral sensors, and control elements.

In turn, the device for washing, drying, and disinfecting device canals (100) for washing and disinfecting the same, can control the entry of the pressurized gas into the pneumatic cylinder (1) by means of the first actuator which can be a solenoid valve (20) which is connected to a computing unit (19), said solenoid valve (20) located before the inlet (3). With the above, the movement of the plunger (7) is precisely controlled to obtain an adequate control in the pressures to be generated in the container (9).

Referring to FIG. 3, in one embodiment of the present disclosure, the computing unit (19) connected to the solenoid valve (20) arranged between the first fluid source which in this case is the gas source (5) and the inlet (3). The computing unit (19) sends an actuation control signal to the solenoid valve (20), said solenoid valve (20) being opened or closed from the actuation control signal.

A control signal shall be understood as the signal that controls a variable of a control element, e.g., in this case the control signal sent to the solenoid valves controls the opening of the solenoid valves.

In one embodiment of the disclosure, when the pneumatic cylinder (1) is double acting, the solenoid valve (20) is a selector valve having one inlet and two outlets, but said valve only allows passage in one way only, i.e., the solenoid valve (20) allows passage of the pressurized fluid which in the preferred embodiment is pressurized gas to the inlet (3A) or the passage of pressurized gas to the inlet (3B).

The computing unit (19) is a device that processes data from an external element, such as a pressure sensor or a position sensor, analyzes it and carries out actions such as generating a signal (e.g., control signal), generating data, accessing stored data, among other possible actions it may carry out.

The computing unit (19) can be selected from the group comprising: microcontrollers (v.gr PSOC 4BLE), microprocessors, DSCs (Digital Signal Controllers), FPGAs (Field Programmable Gate Arrays), CPLDs (Complex Programmable Logic Devices), ASICs (Application Specific Integrated Circuits), SoCs (System on Chip), PSoCs (Programmable System on Chip), computers, servers, tablets, cell phones, mobile phones, and other devices, PSoCs (Programmable System on Chip), computers, servers, tablets, cell phones, smart phones, signal generators, and computing units, processing units or processing modules known to a person ordinarily versed in the subject and combinations thereof. The computing unit (19) may be or include a special purpose programmed processing unit, programmed to carry out the methods of the present disclosure. In a particular example, the computing unit (19) is a microcontroller and a microprocessor wherein the microcontroller carries out the function of receiving data from sensors, activating power elements. On its side, the microprocessor is in charge of receiving the information supplied by the user, storing it in the database and carrying out the methods of the present invention depending on the data supplied by the sensors and the user.

Additionally, the device for washing, drying, and disinfecting device canals (100) has an electrical power source connected to the computing unit (19), said electrical power source being a device capable of maintaining an electrical potential difference between two or more terminals. Such as an alternating current source, direct current source, batteries, photovoltaic source, thermoelectric source, among other devices capable of maintaining an electrical potential difference between two or more terminals and electrical energy sources known to a person ordinarily versed in the matter or combinations thereof.

In one embodiment of the disclosure, the device for washing, drying, and disinfecting device canals (100) can detect the presence of obstructions in the device canal (40) and, further, optionally the device for washing, drying, and disinfecting device canals (100) can remove such obstructions. The detection of obstruction in the device canal (40) is done by obtaining the time in which the cylinder, either the pneumatic cylinder (1) or a hydraulic cylinder, makes its stroke cycle, i.e., how long it takes for the plunger (7) to return to the initial position. In order to obtain the time in which the pneumatic cylinder (1) or hydraulic cylinder makes its stroke cycle, the device for washing, drying, and disinfecting device canals (100) can count on the pressure at which the fluid enters the cylinder and the dimensions of the plunger (7), distance sensors, presence sensors, among others and combinations thereof. In a particular example, the pneumatic device for washing, drying, and disinfecting device canals (100) has at least one presence sensor inside the chamber (2). In the event that any type of sensor is used to know the position of the plunger (7), said sensor will send a plunger position signal (7), which is processed by the computing unit (19) to generate a position data.

In another particular example, the computing unit (19) has as input the data of the pressure at which the fluid enters the cylinder and, has an input data of the geometry of the cylinder and the plunger (7), and with this data generates a plunger position data (7) to estimate the position of the plunger (7) inside the chamber (2). The pressure data may be input to the computing unit (19) or may be generated from a pressure signal sent from a pressure sensor that monitors the pressure of the fluid entering the cylinder.

Referring to FIG. 3, in one embodiment of the disclosure, the chamber (2) has a presence sensor (22) arranged inside said chamber (2) and connected to the computing unit (19), which is configured to obtain a plunger position signal and send said position signal to the computing unit (19), wherein the computing unit generates the actuation control signal from the plunger position signal. In this particular example, by having a single presence sensor (22) it is possible to directly obtain the time in which the pneumatic cylinder (1) makes its stroke cycle. In one embodiment of the invention, the position sensor (22) is configured to detect that the plunger (7) is at a given position which may be the initial position of the stroke cycle. Once the plunger (7) is at said given position, the position sensor (22) sends the plunger position signal. In a particular example, the position sensor (22) is an inductive sensor, which generates the plunger position signal when the plunger (7) is at a preset distance on the inductive sensor. In another particular example, the position sensor (22) is a mechanical switch located in the initial position, in this case when the plunger (7) comes into contact with the mechanical switch, said mechanical switch generates the plunger position signal (7).

On the other hand, in a particular example the device for washing, drying, and disinfecting device canals (100) can additionally and directly obtain the time in which the plunger (7) makes half a stroke cycle, i.e., the time since the plunger (7) starts from the initial position until it reaches its final stroke position.

Referring to FIG. 4, in one embodiment of the disclosure, the chamber (2) has a first position sensor (22A), arranged within the chamber (2) at an upper end of the chamber (2); and a second position sensor (22B), arranged within the chamber (2) at a lower end of the chamber (2). Said first and second position sensors (22A, 22B) are configured to obtain a first plunger position signal and a second plunger position signal and send said first and second position signals to the computing unit (19). Wherein the computing unit (19) generates the solenoid valve control signal from the first plunger position signal and the second plunger position signal. One of the technical effects of using two position sensors is to have a higher accuracy in the measurement of the displacement times of the piston rod (6). In addition, to ensure that the measurement is being carried out in the ascent and descent of the piston rod (6).

On the other hand, the device for washing, drying, and disinfecting device canals (100) can control the inflow of the pressurized gas into the device canal (40) for drying. By means of the second actuator which is a solenoid valve (21) that is connected to the computing unit (19), said solenoid valve (21) located upstream of the second connection port (14). With the above, the passage of the pressurized gas is controlled and furthermore, the solenoid valve (21) can control the pressure at which said pressurized gas enters if necessary. One of the technical effects of the above is the guarantee that after disinfection of the canal (40) of the medical device there will be no microbial growth due to humidity, since these devices are exposed to the environment, e.g., when the device to be cleaned is a medical device.

Referring to FIG. 3, in one embodiment of the disclosure, between the gas source (5) and the fourth connection port (16) the solenoid valve (21) is arranged, which is connected to the computing unit (19), wherein the solenoid valve (21) controls the gas passage according to an actuation control signal sent by the computing unit (19).

On the other hand, and as mentioned above, the device for washing, drying, and disinfecting device canals (100) can carry out the drying of the device canal (40) and of the connecting element of the second fluid source (17) and the second connection port (14). For the above, the multi-way valve (12) has the fifth connection port (18), said fifth connection port (18) is connected to the gas source (5), although in one embodiment of the invention and referring to FIG. 3, between the fifth connection port (18) and the gas source (5) the solenoid valve (21) is located.

In order to achieve simultaneous drying of the canal (40) and the fluid source connection element, the multi-way valve (12) is in the third position and the computing unit (19) sends the actuation control signal to the solenoid valve (21). Once the solenoid valve (21) receives the actuation control signal, the solenoid valve (21) allows the pressurized gas coming from the gas source (5) to enter the fourth connection port (16); and exits through the third connection port (15) into the device canal (40); and enters through the fifth connection port (18) and exits through the second connection port (14) into the connection element (40) of the device; and enters through the fifth connection port (18) and exits through the second connection port (14) into the connection element (40) of the device.

In one embodiment of the disclosure, the multi-canal valve (12) is a mechanical multi-canal ball valve such as that shown in FIGS. 2A, 2B, 2C, in this case the first canal ball must move towards the first connection port (13) for the pressurized gas coming from the gas source (5) to enter the second connection port (14). For this purpose, at the same time that the solenoid valve (21) is activated, the computing unit (19) sends an actuation control signal to the solenoid valve (20), which, once received by the solenoid valve (20), allows the pressurized gas to pass to the pneumatic cylinder (1). The pneumatic cylinder is activated in such a way that the piston (8) moves upwards so that the ball inside the first multi-way valve canal (12) moves towards the first connection port (13). In this way, the pressurized gas entering through the fifth additional port (18) exits through the second connection port (14) to the connection element of the second fluid source (17).

Optionally, the device for washing, drying, and disinfecting device canals (100) can detect leaks in the canal of the medical device, where a leak test is carried out on it. The tightness test is carried out by opening the solenoid valve (21) to allow the passage of pressurized gas into the device canal (40) until a certain pressure is reached inside the canal (40). Once, the determined pressure is reached, the solenoid valve (21) is closed, and it is determined whether the pressure is decreased for a predetermined time. In case the pressure decreases, this means that the device canal (40) is leaking. For internal pressure measurement, the pneumatic device for washing, drying, and disinfecting device canals (100) can have a pressure sensor, which can be located where the canal (40) is connected to the third connection port (15) or at some point of the multi-way valve (12) that allows this measurement, e.g., the fourth connection port (16).

In order to carry out leak detection in the canal (40) of the medical device, the canal (40) must be closed to achieve the internal pressure increase, in some of the medical devices the canals (40) are already closed. However, in the case that the canal (40) or canals (40) of the medical device are not closed at the opposite end, where said canal (40) is connected to the third connection port (15) a blocking element (e.g., plug) must be provided. In a particular example, the endoscopes have at least one canal that is closed, and it is on this canal that the leak detection test is carried out.

Referring to FIG. 4, in one embodiment of the invention, a pressure sensor (23) connected to the computing unit (19) is arranged in the fourth connection port (16), which is configured to obtain a pressure data and send said pressure data to the computing unit (19). Said computing unit (19) obtains an actuation control signal from the pressure data received and sends said signal to the solenoid valve (21) to allow and restrict the passage of gas to the fourth connection port (16). The computing unit (19) generates an alarm signal if the pressure data varies within a certain time from the pressure signal.

The pressure sensor (23) can be selected from the group consisting of capacitive pressure sensors, pressure sensors with strain gauge technology, piezoresistive pressure sensors, resistive pressure sensors, resonant pressure sensors, pressure sensors known to a person ordinarily skilled in the art and combinations thereof.

On the other hand, the pneumatic device for washing, drying, and disinfecting device canals (100) can carry out environmental measurements that may affect the fluid used for disinfection, e.g., environmental temperature, humidity, particles per million (ppm), among others. For the above, the computing unit (19) is connected to at least one sensor which is selected from the group consisting of temperature sensors (e.g., thermistor, thermocouple, RTD, non-contact infrared sensors, among others), humidity sensors (e.g., capacitive humidity sensors, resistive humidity sensors, among others), $CO_2$ sensors, $O_2$ sensors, and combinations thereof. In a particular example, the computing unit (19) is connected to a temperature sensor (25) which is a thermistor for measuring temperature (25) and a humidity sensor (26) which is a capacitive humidity sensor. One of the technical effects of adding the temperature sensor (25) and the humidity sensor (26) is that measurements of the ambient conditions can be made and with such measurements it is ensured that the device of the present disclosure and the fluids (e.g., disinfectants) are working under optimal conditions.

Similarly, the pneumatic device for washing, drying, and disinfecting device canals (100) may also have other elements for measuring and/or controlling pneumatic variables, e.g., there may be an additional valve or several additional valves or pressure gauges.

Referring to FIG. 4, between the gas source (5) and the solenoid valve (21) a pressure gauge (35), which allows to know the pressure at which the pressurized air enters the gas source (5) and an additional valve (36) which allows to control the flow of the pressurized gas to the solenoid valve (21) are located. In a particular example, the additional valve (36) is a flow meter. One of the technical effects of using the additional valve (36) is that it allows to control the amount of pressurized gas flowing through the equipment, thus optimizing the pressurized gas used for the operation of the device and the drying of the canals of the medical device.

The pneumatic device for washing, drying, and disinfecting device canals (100) can have additional elements to supply different functionalities associated with the data collected to the computing unit, which may be required, such as display devices, input device, among others.

Optionally, the computing unit (19) is connected to a display device (24), which corresponds to any device that can be connected to a computing unit and display its output. It is selected from CRT (Cathode Ray Tube) monitor, flat panel display, LCD (Liquid Crystal Display), active matrix LCD display, passive matrix LCD display, LED displays, display projectors, TV (4KTV, HDTV, plasma TV, Smart TV), OLED (Organic Light Emitting Diode) displays, AMOLED (Active Matrix Organic Light Emitting Diode) displays, QD (Quantum Dot Display) displays, segment displays, among other devices capable of displaying data to a user, known to the technically savvy, and combinations thereof.

In addition, the computing unit (19) is connected to an input device and/or a Human Interface Device (HID). The HID device includes, without limitation, keyboard, mouse, trackball, touchpad, pointing device, joystick, touch screen, among other devices capable of allowing a user to input data into the computing unit (19) of the device of the present disclosure and combinations thereof.

The computing unit (19) is connected to an external device (29), wherein the computing unit (19) is configured to send data to the external device (29) and receive data from the external device (29).

Referring to FIG. 3, the computing unit (19) is connected to the external device or devices (29) by means of a communications module (27) which is a hardware element coupled a computing unit, processing unit, or processing module or a server. It is configured to establish communication by means of communication links between one or more computing units or servers to exchange data, commands and/or tags. The communication module (27) is selected from the group consisting of wired communication modules, wireless communication modules, and wired and wireless communication modules.

The wireless communications module (27) uses a wireless communication technology that is selected from the group consisting of Bluetooth, WiFi, RF ID (Radio Frequency Identification), UWB (Ultra-Wide Band), CALM (Communications Access for Land Mobile) standard, GPRS, Konnex or KNX, DMX (Digital MultipleX), WiMax and equivalent wireless communication technologies that are known to a person ordinarily versed in the field and combinations thereof.

The wired communications module (27) has a wired connection port that allows communication with external devices through a communications bus, which is selected among others, from the group consisting of I2C (from the acronym of IIC Inter-Integrated Circuit), CAN (Controller Area Network), BUS RS-232, BUS RS-485, BUS-422, BUS-423, Ethernet, SPI (Serial Peripheral Interface), SCI (Serial Communication Interface), QSPI (Quad Serial Peripheral Interface), 1-Wire, D2B (Domestic Digital Bus), Profibus and others known to a person ordinarily versed in the art.

In a particular example, the computing unit (19) is connected to a server via the communications module (27), wherein the server is configured to program the computing unit (19).

A server is a device that has a processing unit configured to execute a series of instructions corresponding to stages or steps of methods, routines, or algorithms. In addition, the server has a communications module that allows connection with other servers or computational devices.

In addition, servers can connect to each other, and connect to other computing devices through web services architectures and communicate via communications protocols such as SOAP, REST, HTTP/HTML/TEXT, HMAC, HTTP/S, RPC, SP, and other communications protocols known to a person ordinarily versed in the art.

Similarly, the servers mentioned in the Specification of the present invention may be interconnected through networks such as the Internet, VPN networks, LAN networks, WAN networks, other equivalent or similar networks known to a person averagely skilled in the art and combinations thereof. These same networks may connect the computing unit (19) to one or more servers.

Some of the servers mentioned in the Specification of the present invention may be virtual servers or physical servers. Any of the servers may include a storage module configured to store operating data sent by the computing unit (19).

On the other hand, the computing unit (19) may be connected to a notification device or more notification devices, said notification device being a piece of hardware that is coupled to a computing unit, processing unit or processing module or a server, which is configured to carry out an action representing an alert message, when an alarm data or alarm signal is received, wherein the action may be to display a message, emit light, vibrate, play a sound, or other action representing an alert message and a combination of the foregoing.

Figure 5:
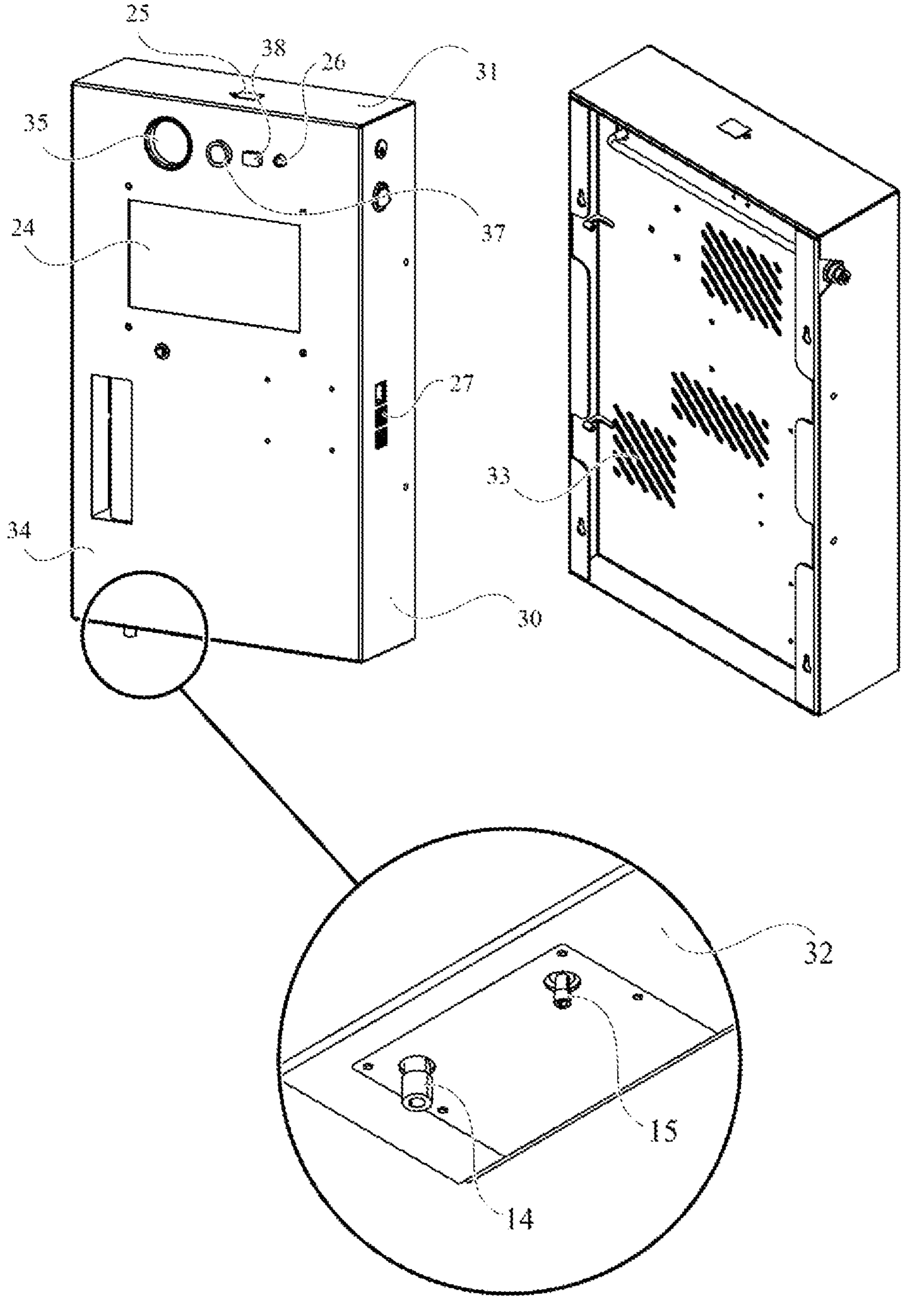
FIG. 5 shows a cabinet housing a pneumatic device for washing, drying, and disinfecting device canals, wherein the device comprises a pressure gauge, a buzzer, a light emitting diode, a temperature sensor, a humidity sensor, a computing unit, and a communications module.

Referring to FIG. 5, in one embodiment of the invention, the device for washing, drying, and disinfecting device canals (100) has three notification devices, which in this case are a light emitting diode (37), a buzzer (38) and a display device which is a touch screen, which allow to present an alert message, when the computing unit (19) sends an alarm signal, this alert message can mean the presence of obstructions or the presence of leaks in the device canal (40) or other type of alert.

The device for washing, drying, and disinfecting device canals (100) can be housed in a cabinet or container, in which the elements of the device are arranged, thus allowing them to be protected from contamination from the environment. In a particular example, the cabinet consists of two side plates, a bottom plate, a top plate, a bottom plate, and a door that is pivotally connected to one of the side plates.

Referring to FIGS. 1 to 6, a cabinet is shown comprising two side plates (30), a top plate (31) and a bottom plate (32), said plates are connected to a bottom plate (33) and a door (34) which is pivotally connected to one of the side plates. The bottom wall (33) is provided with slots, said slots allow cooling the electronic equipment inside the cabinet such as the display device and the computing unit.

With the system and modalities of said system described above, the present invention implements methods by which leaks in the canal of a medical device are detected and, further, obstructions in said canal can be detected and removed.

Referring to FIG. 6, in one embodiment of the disclosure, a method of detecting leaks in medical device canals using the device for washing, drying, and disinfecting device canals (100), comprises:

opening a second actuator upon receiving an actuation control signal sent by a computing unit (19), said second actuator arranged between a gas source (5) and a fourth connection port (16) of a multi-way valve (12), obtaining a pressure data by means of a pressure sensor (23) located in the fourth connection port (16) and sending it to the computing unit (19), the pressure sensor (23) is connected to the computing unit (19);

closing the second actuator to stop supplying gas coming from the gas source (5) by means of a signal sent by the computing unit (19), the computing unit (19) sending the signal when the pressure data matches a predetermined pressure data previously stored in the computing unit (19);

generating an alarm signal by means of the computing unit (19), if the pressure data varies within a predetermined time after the closing of the second actuator.

Particularly, when executing the leak detection method, the multi-way valve (12) is in a third position, which allows the passage of the gas coming from the gas source (5) into the device canal (40).

Opening the Second Actuator

The method of detecting leaks in medical device canals first allows the entry of pressurized gas into the medical device canal, which is achieved by opening the second actuator which may be the solenoid valve (21) and having the multi-way valve (12) in the third position. In one embodiment of the disclosure, at the stage of opening the solenoid valve (21), additionally the computing unit (19) sends a control signal to the multi-way valve (12), in this embodiment the multi-way valve (12) has an actuator that is activated upon receiving said control signal.

Obtaining Pressure Data

In one embodiment of the invention, once the second actuator is open, which may be the solenoid valve (21), a pressure measurement is made by means of the pressure sensor (23) located in the fourth connection port (16) of the multi-way valve (12), being the device canal (40), this pressure measurement corresponds to the internal pressure of the device canal (40). The measured pressure corresponds digitally to the pressure data provided by the pressure sensor (23), this pressure data is sent to the computing unit (19), which carries out a processing of this data.

Closing the Second Actuator

The computing unit (19) processes the pressure data sent by the pressure sensor (23); such processing corresponds to the comparison of the pressure data with a predetermined pressure data. Once the value of the pressure data corresponds to the value of the predetermined pressure data, the computing unit (19) sends an actuation control signal to the second actuator, whereupon said second actuator closes. In an embodiment of the invention, the computing unit (19) sends an actuation control signal to the solenoid valve (21), whereupon said solenoid valve (21) closes.

Generating an Alarm Signal

After closing the second actuator which can be the solenoid valve, the pressure sensor (23) continues sending the pressure data to the computing unit (19), in this case the computing unit (19) generates the control signal if the pressure data varies in a predetermined time that is stored in the computing unit (19). In case the computing unit (19) detects variation in the pressure data, it means that there is a leak in the endoscope, when this happens the computing unit is configured to generate the alarm signal. To avoid false alarms, the computing unit (19) can be configured so that when it is processing the variation, it has a tolerance, such tolerance can be in the range of 0.1% and 7%. In a particular example, the computing unit (19) is configured to have a tolerance of 5% when processing the variation.

Once the alarm signal is generated it may optionally be sent to the notification device or to the various notification devices that may comprise the device for washing, drying, and disinfecting device canals (100) to display an alert message. On the other hand, the alarm signal is optionally sent to the display device (24), which displays an alert message.

Optionally, the leak detection method may have an additional stage, in which the computing unit (19) controls the gas pressure, coming from the gas source (5), so that the predetermined pressure data is reached in a filling time, wherein the computing unit (19) has stored the filling time. This means that the computing unit (19) controls the flow or pressure of the gas entering the device canal (40) so that the internal pressure increases in a controlled manner and becomes equal to the predetermined pressure at the required filling time.

In one embodiment of the disclosure for controlling the pressure of the gas coming from the gas source (5), the computing unit (19) sends an actuation control signal to the second actuator which may be the solenoid valve (21), so that said solenoid valve (21) according to its opening regulates the flow or the pressure of the pressurized gas that said solenoid valve (21) lets pass. In another embodiment of the disclosure for controlling the flow of the gas coming from the gas source (5) and referring to FIG. 4, between the gas source (5) and the solenoid valve (21) the additional valve (36) can be arranged to control the flow of the pressurized gas which is sent to the solenoid valve (21). In this case, the computing unit (19) sends a control signal to the additional valve (36) to set the pressure or flow that the pressurized gas sent to the canal of the medical device must have to achieve the predetermined pressure data in the filling time set in the computing unit (19).

Preferably, the filling time is in a range of 5 seconds to 2 minutes, even more preferably the filling time is in a range between 15 seconds to 45 seconds. In a particular example, the filling time is 30 seconds.

As mentioned above, another aspect of the present disclosure relates to a method of clog detection and removal. This is accomplished by measuring the time it takes for the pneumatic cylinder (1) to make one stroke cycle.

Figure 7:
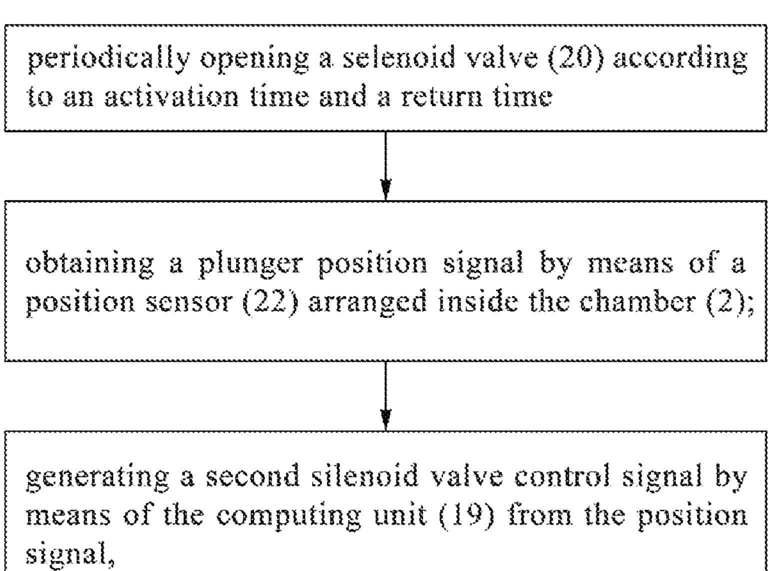
FIG. 7 shows a flow diagram of a method of detecting device canal obstructions.

Referring to FIG. 7, in one embodiment of the disclosure, the method of detecting obstructions in endoscopes using the device for washing, drying, and disinfecting device canals (100), comprises:

periodically opening a first actuator according to an activation time and a return time, starting from a first actuation control signal sent by a computing unit (19) connected to the first actuator, wherein said first actuator is located between the inlet (3) and the gas source (5);

obtaining a plunger position signal by means of a position sensor (22) arranged inside the chamber (2), said plunger position signal being obtained when the plunger (7) is in a given position inside the chamber (2); and generating a second actuation control signal by means of the computing unit (19) from the position signal.

Particularly, the opening of the first actuator allows the entry of gas coming from the gas source (5), which generates a gas pressure difference inside the chamber (2) to generate an up and down movement of the plunger (7). Additionally, the second actuation control signal decreases the activation time, thereby increasing the moving speed of the plunger (7) and in turn of the piston rod (6) and piston (8), thereby increasing the pressure exerted on the fluid entering through the endoscope inlet, thus freeing the obstructions.

The activation time is to be understood as the time in which the first actuator, which may be the solenoid valve (21), is open to allow the gas coming from the gas source (5) to move the plunger (7) from the initial position to the final position. The return time is to be understood as the time in which the plunger (7) moves from the end position to the initial position.

Periodical Opening a First Actuator According to an Activation Time

In case the pneumatic cylinder (1) is single acting, the computing unit (19) sends the first actuation control signal to the first actuator which can be the solenoid valve (20), said first actuation control signal tells the solenoid valve (20) to open for the activation time. After said activation time elapses, the computing unit (19) stops sending the first actuation control signal and the solenoid valve (20) closes. In this type of pneumatic cylinders and as mentioned above, there is an elastic element inside the chamber (2) and connected to the plunger (7), said elastic element is configured to return the plunger (7) to its initial position in a return time, said return time is previously stored in the computing unit (19). Once this return time has elapsed, the computing unit (19) sends again the first control signal to the solenoid valve (20) and the latter opens for the activation time and repeats the cycle described above.

On the other hand, in case that the pneumatic cylinder (1) is double acting, the computing unit (19) sends a control signal to the first actuator which can be the solenoid valve (20). In this case the solenoid valve (20) is a two-way solenoid valve, so one of its ways is opened during an activation time to allow the passage of the pressurized gas coming from the gas source (5) to the inlet (3A) of the pneumatic cylinder (1). As the gas enters the inlet (3A), the piston (7) moves from the initial position to the final position. Then, the computing unit (19) sends another control signal to the solenoid valve (20) to open the other way for a return time to allow the passage of pressurized gas from the gas source (5) to the inlet (3B) of the pneumatic cylinder (1). When the gas enters the inlet (3*b*), the piston (7) moves from the end position to the initial position, thus ending the stroke cycle. Once this return time has elapsed, the computing unit (19) sends the control signal to the solenoid valve (20) again, which opens for the activation time and repeats the cycle described above.

Obtaining Pressure Data

In a particular example, the computing unit (19) has a pressure data indicating the pressure at which the fluid enters the cylinder, either the pneumatic cylinder (1) or a hydraulic cylinder. Additionally, the computing unit (19) knows the geometry data of the chamber (2) and the plunger (7) and with these data the computing unit (19) determines the position of the plunger (7) inside the chamber (2).

In another particular example, the chamber (2) inside has the position sensor (22) or position sensors (22A, 22B), each position sensor (22, 22A, 22B) sends the position signal when each sensor (22, 22A, 22B) detects the plunger (7). Each position sensor (22, 22A, 22B) detects that the plunger (7) is at a predetermined position within the chamber (2) such as the home position and/or the end position of the stroke cycle. When only the position sensor (22) is present, which in one embodiment of the disclosure is located at the initial position, with the plunger position signal sent by it, the computing unit (19) obtains a position data of the plunger (7). The computing unit (19) with the plunger position data can determine how long it takes for the plunger (7) to carry out the stroke cycle, in this case the computing unit (19) determines how much time elapses for the position sensor (22) to send two position signals in a row.

On the other hand, when there is a position sensor (22A) that can be located at the initial position of the stroke cycle and a position sensor (22B) that can be located at the final position of the stroke cycle, the computing unit (19) obtains position data from the plunger position signals (7) sent by the plunger position sensors (22A, 22B). The computing unit (19) obtains some position data from the plunger position signals (7) sent by the position sensors (22A, 22B). The computing unit (19) from the obtained position data can determine how long it takes the plunger (7) to carry out half a stroke cycle, in this case the computing unit (19) determines how much time elapses between the reception of the position signal from the position sensor (22A) and the position signal from the position sensor (22B).

Generating a Second Actuation Control Signal

The computing unit (19) receives from the position sensor (22) or position sensors (22A, 22B) at least one position signal of the plunger (7) with which the second control signal is generated, with said position signal or position signals the computing unit (19) obtains the position data of the plunger (7). In particular, with the position data it is possible to determine how long it takes the plunger (7) to carry out a stroke cycle.

Optionally, the computing unit (19) from the position data determines a cycle time which refers to the time taken by the plunger (7) to carry out one stroke cycle.

Once the cycle time is calculated, it is compared with a predetermined cycle time. In particular, the computing unit (19) checks whether the cycle time is greater than the pneumatic cycle time and, if so, then the second actuation control signal is generated.

Once the second actuation control signal is generated, the computing unit may generate a second alarm signal, said second alarm signal may optionally be sent to the notification device or to the different notification devices that may comprise the device for washing, drying, and disinfecting device canals (100) to display an alert message. On the other hand, the second alarm signal optionally is sent to the display device (24), which displays an alert message.

As mentioned above, the second actuation control signal decreases the cycle time by increasing the incoming fluid pressure, thereby moving the plunger (7) faster.

EXAMPLE

A device for washing, drying, and disinfecting device canals was designed, which in this case is a medical device that is an endoscope, the features of the medical device are as follows:

For this particular example, the pneumatic cylinder (1) was double acting, so the chamber (2) had an inlet (3A) and a second inlet (3B). In addition, between the gas source (5), which in this case was the central air supply of a hospital and the inlets (3A, 3B) a first actuator was located, which was a solenoid valve (20), which was a solenoid selector valve with silencers with one inlet and two outlets, where the outlets are connected to the inlets (3A, 3B). Position sensors (22A, 22B) are arranged internally in the chamber (2), wherein the position sensors (22A, 22B) are inductive sensors.

The piston rod (6) of the pneumatic cylinder (1) has at one end a piston (8) and said piston (8) is arranged inside the container (8), which is formed in glass.

The container (9) is connected to the multi-way valve (12), which is a mechanical multi-way valve with five connection ports. Similarly, between the gas source (5) and the fourth connection port (16) and the fifth connection port (18) of multi-way valve (12) a second actuator which is a solenoid valve (21) is located, which is a closing/opening solenoid valve. A pressure sensor (23) is located in the fourth connection port (16), wherein the pressure sensor (23) is a piezoresistive silicon sensor.

The solenoid valve (20), the second solenoid valve (21), position sensors (22A, 22B) are connected to the computing unit (19): which comprises a processor with 64-Bit architecture, (Broadcom BCM2711 quad-core ARM A72 processor with VIDEOCORE VI 3D GPU, PCIs bus for connection of 4 USB 3.0 ports, Ethernet controller, LPDDR4 RAM memory speed 2,400 MHZ DE 8 GB storage).

The computing unit (19) is connected to a display device (24) which is a 7" LCD multi-touch capacitive touch screen, TFT type with DSI interface, resolution 1024×600 pixels, color depth 24 bits with HDMI connection and two notification devices which are a light emitting diode (37) and a buzzer (38). Additionally, the computing unit (19) is connected to a temperature sensor (25) which is a thermistor and a humidity sensor (26) which is a capacitive humidity sensor.

With the above configuration, it was possible to clean, disinfect, and dry one of the endoscope canals where the device saves space and energy efficiency.

It shall be understood that the present invention is not limited to the embodiments described and illustrated above, for as will be evident to a person skilled in the art, there are possible variations and modifications which do not depart from the invention spirit defined by the following claims.

The invention claimed is:

1. A pneumatic device for washing, drying, and disinfecting device canals, comprising:

a cylinder comprising:

a chamber with a inlet and an outlet, said inlet configured to connect with a first fluid source;

a piston rod connected to the outlet of the chamber; and a plunger arranged on the piston rod, said plunger being located inside the chamber;

a piston connected to one end of the piston rod;

a container (9) with an inlet and an outlet, said inlet being aligned with the outlet of the chamber of the cylinder and wherein the piston is located inside the container; and, a multi-way valve with four connection ports, a first connection port (13) configured to connect to the outlet of the container, a second connection port configured to connect to a second fluid source; a third connection port configured to connect to a canal of a device; and a fourth connection port configured to connect to the first fluid source, wherein the inlet of the chamber allows the entry of a fluid coming from the first fluid source into the chamber generating a fluid pressure difference inside the chamber to generate an up and down movement of the plunger;

wherein, the multi-way valve in a first position allows the passage of fluid from the second fluid source into the container, in a second position the multi-way valve allows the passage of fluid from the container into the device canal, and in a third position the multi-way valve allows the passage of fluid from the first fluid source into the device canal (40) and wherein the multi-way valve is a mechanical multi-way valve with balls, the interior of the mechanical multi-way valve comprising canals, which are sealed with balls that move according to the current of the fluid flow entering through the connection ports, allowing the fluid flow to move in one direction depending on the position of the balls.

2. The device according to claim 1, wherein between the first fluid source and the inlet of the chamber a valve is arranged, and between the first fluid source and the fourth connection port a valve is arranged.

3. The device according to claim 2, wherein each valve is selected from the group consisting of solenoid valves, ball valves, check valves, gate valves, safety or pressure relief valves, globe (or poppet) valves, butterfly valves, diaphragm valves, rotary valves, rotary valves, non-return valves, such as swinging flap valves, spring valves, piston valves, ball check valves, knife gate valves, regulating and control valves and combinations thereof.

4. The device according to claim 1, wherein the multi-way valve has a fifth connection port connected to the first fluid source, wherein the multi-way valve has a fourth position, wherein the fluid enters through the fifth connection port and exits through the second connection port.

5. The device according to claim 1, further comprising a computing unit connected to a solenoid valve arranged between the first fluid source and the inlet of the chamber; wherein the computing unit sends an actuation control signal to the solenoid valve, said solenoid valve being opened or closed from the actuation control signal.

6. The device according to claim 5, wherein the chamber has a position sensor arranged inside said chamber and connected to the computing unit, the position sensor being configured to obtain a plunger position signal and send said position signal to the computing unit, wherein the computing unit (19) generates the actuation control signal from the plunger position signal.

7. The device according to claim 5, wherein the chamber has a first position sensor arranged inside the chamber at an upper end of the chamber and a second position sensor arranged inside the chamber at a lower end of the chamber (2), said first and second position sensors are configured to obtain a first plunger position signal and a second plunger position signal and send said first and second plunger position signals to the computing unit, wherein the computing unit, generates the solenoid valve control signal from the first plunger position signal and the second plunger position signal.

8. The device according to claim 5, wherein between the first fluid source and the fourth connection port a solenoid valve is arranged, which is connected to the computing unit, wherein the solenoid valve controls the fluid passage according to an actuation control signal sent by the computing unit.

9. The device according to claim 8, wherein the fourth connection port is provided with a pressure sensor connected to the computing unit, the pressure sensor being configured to obtain a pressure data and send said pressure data to the computing unit, wherein the computing unit obtains the actuation control signal from the received pressure data and sends the actuation control to the solenoid valve to allow and restrict the passage of fluid to the fourth connection port, and generate an alarm signal if the pressure data varies within a certain time from the pressure signal.

10. A method of detecting leaks in medical device canals using the device for washing, drying, and disinfecting device canals of claim 1, comprising:

opening a second actuator upon receiving an actuation control signal sent by a computing unit, said second actuator arranged between the first fluid source and a fourth connection port of a multi-way valve, obtaining a pressure data from the computing unit, by means of the pressure sensor which is connected to the computing unit;

closing the second actuator to stop supplying fluid from the first fluid source by means of a signal sent by the computing unit, the computing unit sending the signal when the pressure data matches a predetermined pressure data previously stored in the computing unit;

generating an alarm signal by means of the computing unit, if the pressure data varies within a predetermined time after the first actuator is closed, wherein the multi-way valve is in a third position, which allows the passage of the fluid coming from the first fluid source into the device canal.

11. The method according to claim 10, wherein the computing unit controls the fluid pressure coming from the first fluid source, in a further step, so that the predetermined pressure data is reached within a filling time, wherein the computing unit has the filling time stored.

12. The method according to claim 10, wherein the predetermined time is 30 seconds.

13. A method of detecting obstructions in device canals using the device for leak-testing, cleaning, disinfecting, and drying of device canals of claim 1, comprising:

periodically opening a first actuator according to an activation time and a return time, starting from a first actuation control signal sent by a computing unit connected to the first actuator, wherein said first actuator is located between the inlet of the chamber and the first fluid source;

obtaining a position data of the plunger by means of the computing unit; and generating a second actuation control signal by means of the computing unit from a cycle time obtained from the position data, wherein the opening of the first actuator allows the entry of fluid coming from the first fluid source, which generates a fluid pressure difference inside the chamber to generate an up and down movement of the plunger; and wherein, the second actuation control signal decreases the activation time, thereby increasing the moving speed of the plunger and in turn of the piston rod and piston, thereby increasing the pressure exerted on the fluid entering through the inlet of the device canal (40), thereby releasing the obstructions.

14. The method according to claim 13, wherein the cycle time is determined from the position data, which refers to the time taken by the plunger to carry out one stroke cycle, then compared to a predetermined cycle time, wherein, if the cycle time is greater than the predetermined cycle time, then the second actuation control signal is generated.

* * * * *